United States Patent [19]
Solar

[11] Patent Number: 6,004,328
[45] Date of Patent: Dec. 21, 1999

[54] RADIALLY EXPANDABLE INTRALUMINAL STENT AND DELIVERY CATHETER THEREFORE AND METHOD OF USING THE SAME

[76] Inventor: Ronald J. Solar, 12495 Figtree St., San Diego, Calif. 92131

[21] Appl. No.: 08/878,610

[22] Filed: Jun. 19, 1997

[51] Int. Cl.[6] .................................................. A61B 17/00
[52] U.S. Cl. ........................................... 606/108; 604/271
[58] Field of Search ............................. 604/271; 606/108

[56] References Cited

U.S. PATENT DOCUMENTS

| | | | |
|---|---|---|---|
| 4,271,839 | 6/1981 | Fogarty et al. | |
| 4,732,152 | 3/1988 | Wallsten et al. | 623/1 X |
| 4,848,343 | 7/1989 | Wallsten et al. | 604/271 |
| 4,863,440 | 9/1989 | Chin | 604/271 |
| 5,102,417 | 4/1992 | Palmaz | 606/195 |
| 5,108,416 | 4/1992 | Ryan et al. | 606/194 |
| 5,195,984 | 3/1993 | Schatz | 606/195 |
| 5,275,622 | 1/1994 | Lazarus et al. | 623/1 |
| 5,318,588 | 7/1994 | Horzewski et al. | 606/198 |
| 5,344,426 | 9/1994 | Lau et al. | 606/198 |

Primary Examiner—Michael H. Thaler
Attorney, Agent, or Firm—Robert D. Buyan; Stout, Uxa, Buyan & Mullins, LLP

[57] ABSTRACT

As delivery catheter for a radially expandable intraluminal stent. The delivery catheter comprises an elongate outer tube defining proximal and distal ends and a lumen extending longitudinally therethrough. In addition to the outer tube, the delivery catheter includes an elongate inner tube defining proximal and distal ends and a guidewire lumen extending longitudinally therethrough. The inner tube is movably disposed within the lumen of the outer tube. The delivery catheter further includes a flexible deployment sleeve having a first end attached to the distal end of the outer tube, and a second end attached to the inner tube at a location proximal to the distal end thereof. The pressurization of the lumen of the outer tube with a fluid causes fluid pressure to be exerted on the sleeve in a manner facilitating the movement and the inner and outer tubes relative to each other such that a distal portion of the inner tube extending distally from the second end of the sleeve is deployed from the distal end of the outer tube.

31 Claims, 4 Drawing Sheets

RADIALLY EXPANDABLE INTRALUMINAL STENT AND DELIVERY CATHETER THEREFORE AND METHOD OF USING THE SAME

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by any one of the patent disclosure, as it appears in the Patent and Trademark Office patent files or records, but otherwise reserves all copyright and trade dress rights whatsoever.

FIELD OF THE INVENTION

The present invention pertains generally to medical devices, and more particularly to a radially expandable intraluminal stent device and delivery catheter therefore.

BACKGROUND OF THE INVENTION

The term "stent" is generally used to describe radially expandable endoluminal devices which are implanted within luminal anatomical passageways (e.g., blood vessels, gastrointestinal tract, genitourinary tract, endocrine ducts, etc. . . . ) of the body to, i.) maintain the patency or state of dilation of the passageway, ii.) reinforce the passageway, or iii.) anchor a tubular graft or other object within the passageway.

Typical cardiovascular applications of stents are to maintain dilation and patency of an occluded region of blood vessel, or to bridge a weakened or aneurysmic region of blood vessel. On the other hand, some typical non-vascular applications of such stents are for the treatment of constrictions or injuries to the gastrointestinal tract (e.g., esophagus), ducts of the biliary tree (e.g., common bile duct) or anatomical passageways of the genitourinary tract (e.g., ureter, urethra fallopian tube, etc.).

Transluminally implantable stents are initially disposed in a compact configuration of relatively small diameter, and are mounted upon or within a delivery catheter to facilitate insertion and transluminal advancement of the stent into the desired anatomical passageway. Thereafter, such stents are radially expanded to a larger operative diameter which is equal to or slightly larger than the diameter of the anatomical passageway in which the stent is to be implanted. When radially expanded to such operative diameter, the stent will typically become released or separated from the delivery catheter and anchored or frictionally engaged to the surrounding wall of the anatomical passageway.

Some stents have a pliable, continuous tubular covering, in which case they are typically referred to as a "stented graft" or "stent-graft."

In general, stents and stented grafts fall into two major categories—a) self-expanding and b) pressure-expandable. Those of the self-expanding variety may be formed of resilient or shape memory material (e.g., spring steel or nitinol™) which is capable of self-expanding from its first (radially compact) diameter to its second (operative) diameter without the exertion of outwardly-directed force against the stent or stented graft. Examples of such self-expanding stents and stented grafts are set forth in U.S. Pat. Nos. 4,655,771 (Wallsten, et al.); 4,954,126 (Wallsten); 5,061,275 (Wallsten, et al.); 4,580,568 (Gianturco); 4,830,003 (Wolf, et al.); 5,035,706 (Gianturco, et al.); 5,330,400 (Song) and 5,354,308 (Simon, et al.) and Foreign Patent Publication Nos. WO94/12136; WO92/06734 and EPA183372. Those of the pressure-expandable (i.e., "passive expandable") variety may be formed of plastically deformable material (e.g., stainless steel) which is initially formed in its first (radially compact) diameter and remains stable in such first diameter until such time as outwardly directed pressure is exerted upon the stent or stented graft to cause it to undergo radial expansion and resultant plastic deformation to its second (operative) diameter. Examples of such pressure-expandable stents and stented grafts are set forth in U.S. Pat. Nos. 5,135,536 (Hillstead); 5,161,547 (Tower); 5,292,331 (Boneau); 5,304,200 (Spaulding); 4,733,665 (Palmaz); 5,282,823 (Schwartz, et al.); 4,776,337 (Palmaz); and 5,403, 341 (Solar) and Foreign Patent Publication Nos. EPA480667; and WO95/08966.

In many applications, careful positioning and sound anchoring of the stent or stented graft is critical to the successful treatment of the underlying medical problem. In this regard, the delivery catheter which is utilized to insert and position the stent or stented graft may be an important aspect of the overall system. Various types of delivery catheters for stents and stented grafts have been previously known, including those described in U.S. Pat. Nos. 4,665, 918 (Garza, et al.); 4,733,665 (Palmaz); 4,739,762 (Palmaz); 4,762,125 (Leiman, et al.); 4,776,337 (Palmaz); 4,838,269 (Robinson, et al.); 4,994,071 (MacGregor); 5,037,427 (Harada, et al.); 5,089,005 (Harada); 5,102,417 (Palmaz); 5,108,416 (Ryan, et al.); 5,141,498 (Christian); 5,181,920 (Mueller, et al.); 5,195,984 (Schatz); 5,201,901 (Harada, et al.); 5,269,763 (Boehmer, et al.); 5,275,622 (Lazarus, et al.); 5,290,295 (Querals, et al.); 5,306,294 (Winston, et al.); 5,318,588 (Horzewski, et al.); 5,344,426 (Lau, et al.); 5,350, 363 (Goode, et al.); 5,360,401 (Turnland); 5,391,172 (Williams, et al.); 5,397,345 (Lazarus); 5,405,380 (Gianotti, et al.); 5,443,452 (Hart, et al.); 5,453,090 (Martinez, et al.); 5,456,284 (Ryan, et al.); and 5,456,694 (Marin, et al.) and Foreign Patent Publication Nos. EP-0308-815-A2; EP-0335-341-A1; EP-364-787-A; EP-0442-657-A2; EP-482976-A; EP-0505-686-A1; EP-0611-556-A1; EP-0638-290-A1; WO94/15549; WO95/01761; GB2196-857-A; DE3042-229; and DE3737-121-A.

None of the previously-known delivery catheter systems have been clearly optimal for all types of stents and stented grafts. Accordingly, there remains a need in the art for a design and development of improved delivery catheter systems for at least some types of stents and stented grafts.

SUMMARY OF THE INVENTION

In accordance with the present invention, there is provided a delivery catheter for delivering a radially expandable intraluminal or endoluminal device (e.g., a stent or stented graft) to an intracorporeal location. The delivery catheter generally comprises an inner tube coaxially disposed within an outer tubes, with a fluid-tight, flexible sleeve connecting the distal portion of the inner tube to the distal end of the outer tube. The radially expandable endoluminal apparatus is initially mounted on a distal portion of the inner tube, in a non-expanded condition. At least a portion of the inner or outer tube is axially moveable relative to the other, such that by changing the pressure of fluid within the lumen of the outer tube, the delivery catheter will be caused to transition from a.) a first configuration wherein the distal portion of the inner tube having the endoluminal apparatus mounted thereon is positioned within the lumen of the outer tube, to b.) a second configuration wherein the distal portion of the inner tube having the endoluminal apparatus mounted thereon extends out of and beyond the distal end of the outer tube. After the delivery catheter has been transitioned to its second configuration, the radially expandable endoluminal apparatus my then be radially expanded into contact with the surrounding wall of a luminal anatomical structure within which the delivery catheter has been inserted. Thus, in the preferred method of operation, the delivery catheter is initially deployed in its first configuration during insertion and transluminal advancement to the desired implantation site. Then, after the delivery catheter has been properly positioned relative to the implantation site, the operator will increase the pressure of fluid within the lumen of the outer tube, thereby shifting the catheter to its second configuration, and causing the radially expandable endoluminal apparatus to become uncovered by the outer tube and capable of being radially expanded into contact with the wall of the luminal anatomical structure within which it is positioned. The endoluminal apparatus mounted on the delivery catheter may be of either a self-expanding or pressure-expandable type. In embodiments wherein the endoluminal apparatus is of the self-expanding variety it may simply be released and allowed to self-expand after the catheter has been transitioned to its second configuration. In other embodiments wherein the endoluminal apparatus is of the pressure-expandable variety, a balloon or other pressure exerting apparatus will be utilized to pressure-expand the endoluminal apparatus after the catheter has undergone the transition to its second configuration.

Further in accordance with the invention, the delivery catheter may be of an "over-the-wire" type or a "rapid exchange" type. In embodiments of the over-the-wire type, the inner tube of the delivery catheter extends substantially all the way through the outer tube (and through the proximal connector, if present) such that when a guidewire is passed through the lumen of the inner tube, such guidewire will reside within substantially the entire length of the delivery catheter. In these over-the-wire embodiments the inner tube may be axially slidable or moveable relative to the outer tube, and neither the inner or outer tube need be of variable length. In embodiments of the rapid exchange type, the inner tube will extend through only a distal portion of the outer tube, and a guidewire passage aperture is formed in the sidewall of the outer tube. The proximal end of the inner tube is attached to the wall of the outer tube, at the location of the guidewire passage aperture, such that the guidewire passage aperture opens directly into the lumen of the inner tube, and when a guidewire is advanced through the lumen of the inner tube such guidewire will reside only within a distal portion of the delivery catheter (i.e. that portion between the guidewire passage aperture and the distal end). In these rapid exchange embodiments, one of the inner and outer tubes is of variable length and the other is of fixed length so as to allow the catheter to transition from its first configuration to its second configuration while the proximal end of the inner tube remains firmly attached to the wall of the outer tube. Such variability in the length of either the inner or outer tube may be accomplished by forming a collapsible (e.g., pliable, foldable, accordion-like, telescoping, etc.) segment within one of the tubes. In embodiments wherein the outer tube has a collapsible segment which is weak or laterally deformable (e.g., a flexible or accordion-like segment), a stiffening element such as a wire may be disposed within the lumen of the outer tube to prevent unwanted lateral deformation or bending. Optionally, such stiffening member may be connected to the outer tube, distal to the collapsible segment, and may be pulled in the proximal direction concurrently with pressurization of the outer tube to facilitate retraction of the outer tube and transitioning of the delivery catheter from its first configuration to its second configuration.

Further in accordance with the invention, the delivery catheter may incorporate a proximal connector assembly comprising a rigid body on the proximal end of the delivery catheter having a fluid inlet/outlet port in communication with the lumen of the outer tube, for infusing and withdrawing fluid into/out of the lumen of the outer tube. In some embodiments, especially those of the "over-the-wire" type summarized hereabove, the proximal connector assembly may also incorporate a locking member (e.g., a compressible o-ring or seal member) for holding the inner and/or outer tubes in axially stationary position relative to one another. A locking actuator, such as a rotatable knob, may be formed on such proximal connecter to facilitate the locking and unlocking of the axial position(s) of the inner tube relative to the outer tube. In this manner, the locking member may be actuated to hold the catheter in its first configuration during insertion and positioning. Thereafter, the locking member may be deactuated so as to allow the inner catheter or outer catheter to move, relative to the other, to accomplish the desired transition of the delivery catheter to its second configuration. A sidearm may be formed on the proximal connector in communication with the fluid inlet/outlet port to facilitate the desired pressurization and/or depressurization of the outer tube lumen.

Still further in accordance with the invention, for use specifically with delivery catheters of the above-summarized rapid exchange type having i.) a collapsible outer tube and ii.) a stiffening member (e.g., a wire) which extends through the outer tube and is attached to the outer tube, distal to its collapsible segment, there is provided an inflation pump/retractor device. This inflation pump/retractor device is operative to pump fluid into the lumen of the outer tube while simultaneously retracting or pulling the stiffening member in the proximal direction, thereby causing smooth and controlled transitioning of the delivery catheter from its first configuration to its second configuration. This inflation pump/retractor apparatus comprises an outer housing having an outlet port which is connectable to the lumen of the outer tube of the delivery catheter, and which has a first set of threads formed internally on the surface of its inner bore. A rotatable plunger, having a second set of thread formed about its outer surface is inserted into the bore of the housing and threadably engaged with the first set of threads such that rotation of the plunger in a first direction will cause the plunger to advance in the distal direction within the bore of the housing, thereby forcing fluid from the bore of the housing, out of the outlet port, and into the lumen of the outer tube. The stiffening member or wire of the catheter extends through the bore of the housing and at least part way into a passageway which extends longitudinally into the plunger. This passageway formed in the plunger is internally threaded, in a direction opposite that of the first set of threads formed on the inner wall of the housing (i.e., reverse threaded). A threaded bushing is mounted on the outer surface of the stiffening member or wire, and is engaged with reverse threads of the plunger passageway such that, as the plunger is rotatably advanced in the first direction, the reverse threads of the plunger passageway will cause the bushing and the stiffening member or wire to be retracted in the proximal direction. This facilitates smooth and efficient retraction (i.e., shortening) of the outer tube such that the distal portion of the inner tube (having the radially expandable endoluminal apparatus mounted thereon) is no longer surrounded by the outer tube.

Still further in accordance with the invention, there is provided a radially expandable roll-up stent which is useable in conjunction with the above-summarized delivery catheter of the present invention, or with other types of delivery catheters or devices. This roll-up stent comprises a rectangular sheet having first and second longitudinal edges and first and second lateral edges. A plurality of elongate slots are formed in the rectangular sheet, each of said slots defining a longitudinal slot axis. The slots are arranged in a series of rows with the longitudinal slot axes being substantially parallel to each other, and to the longitudinal edges of the sheet. The sheet is rolled about a central axis (which central axis is substantially parallel to the longitudinal edges of the sheet) thereby forming the sheet into a generally tubular roll-up stent which is alternately disposable in i.) a radially collapsed configuration having a first diameter, and ii.) a radially expanded configuration having a second diameter larger than said first diameter. This stent may be formed of resilient or shape memory material so as to self-expand from its radially collapsed configuration to its radially expanded configuration. Alternatively, this stent may be formed of malleable material capable of being initially formed in the radially collapsed configuration and subsequently reshaped and plastically deformed into its radially expanded configuration.

BRIEF DESCRIPTION OF THE DRAWINGS

These, as well as other features of the present invention, will become more apparent upon reference to the drawings wherein.

DETAILED DESCRIPTION OF THE PREFERRED EMBODIMENTS

Figures 1, 2, 9:
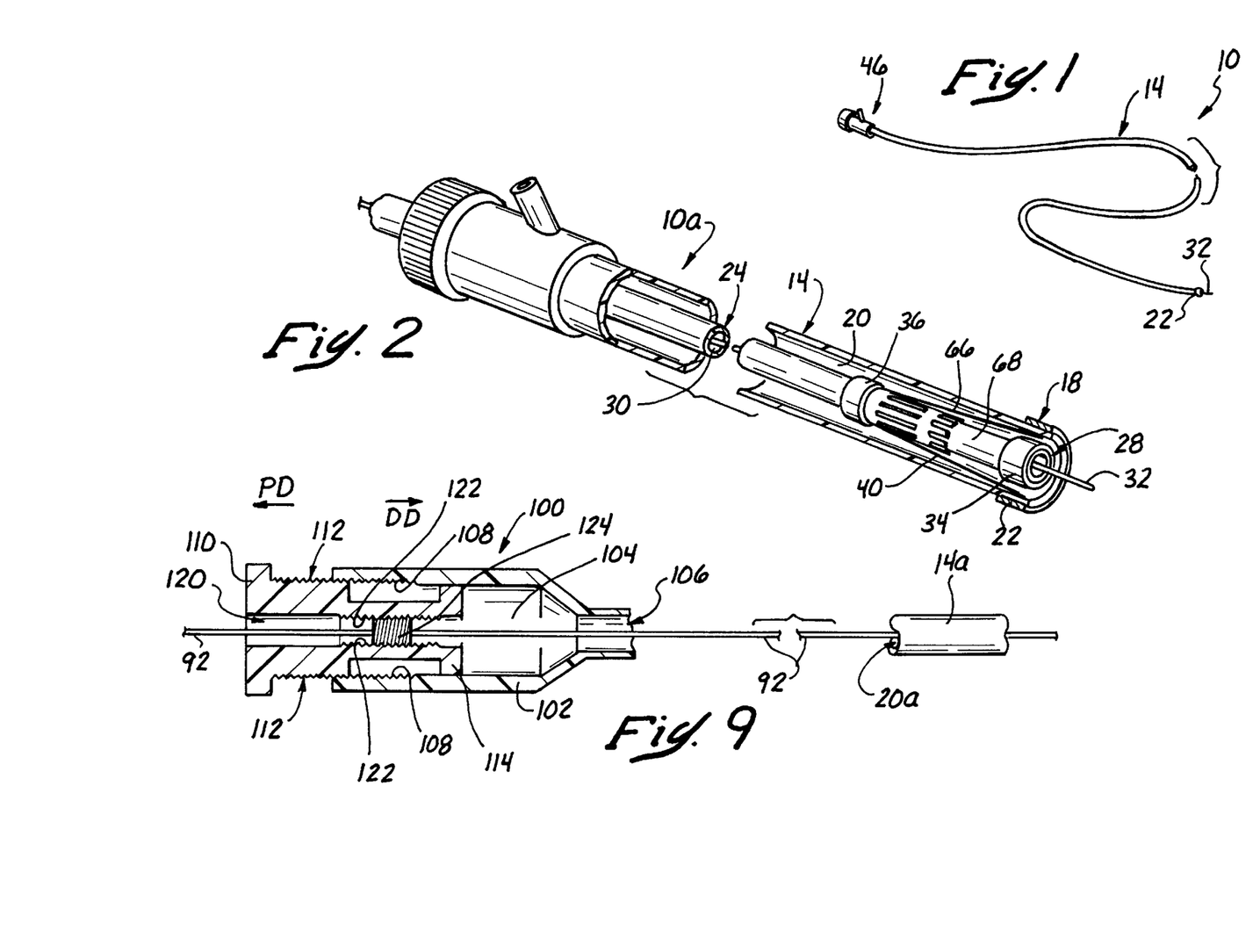
FIG. 1 is a perspective view of the delivery catheter for a radially expandable intraluminal stent constructed in accordance with the present invention.
FIG. 2 is a partial longitudinal-sectional view of the delivery catheter of the present invention.
FIG. 9 is a longitudinal sectional view of an inflation pump/wire retractor device of the present invention which is useable in conjunction with a rapid exchange embodiment of the delivery catheter which incorporates i.) an outer tube having an axially collapsible segment and ii.) a pull wire which extends through the outer tube and is attached to the outer tube at a location distal to its collapsible segment.
Figure 7:
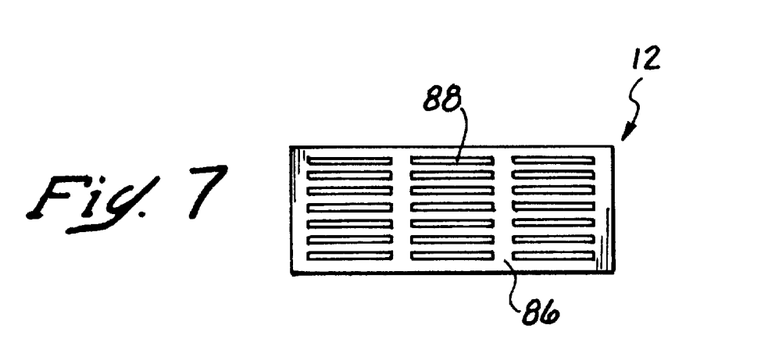
FIG. 7 is a top plan view of a roll-up stent preferably utilized in conjunction with the delivery catheter of the present invention.
Figure 7A:
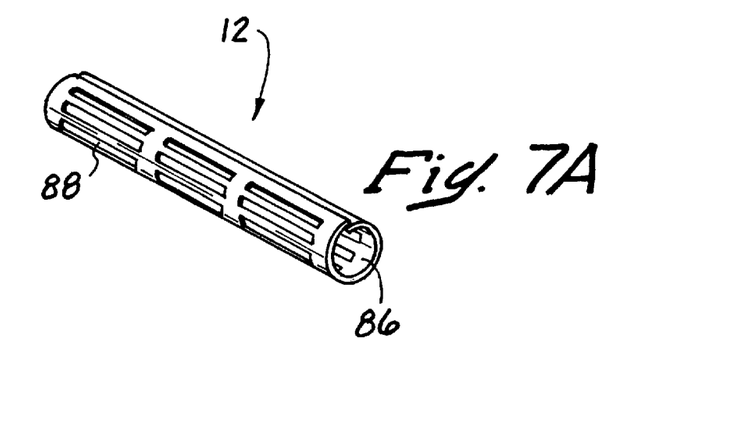
FIG. 7a is a perspective view of the roll-up stent shown in FIG. 7 in its operative, rolled configuration for positioning upon the delivery catheter of the present invention.

Referring now to the drawings wherein the showings are for purposes of illustrating preferred embodiments of the present invention only, and not for purposes of limiting the scope of the invention in any way, FIG. 1 shows a delivery catheter 10 for positioning a radially expandable vascular stent or stented graft into a desired treatment site (e.g., a stenosis) within a blood vessel or other anatomical passageway. As will be discussed in more detail below, the delivery catheter 10 constructed in accordance with the present invention has a very low profile, thus allowing for the advancement thereof through tortuous and/or small diameter anatomical passageways. Radially expandable vascular stents or stented grafts of various designs may be used in conjunction with the delivery catheter 10 of the present invention, including self-expanding stents, balloon expandable stents, or stents which are expandable by other means, such as stents fabricated from shape-memory materials. In the preferred embodiment of the present invention, the delivery catheter 10 is used in conjunction with a self-expanding stent 12 (as shown in FIGS. 7 and 7a), the precise structure of which will be discussed in more detail below.

i. Over-The-Wire Embodiments of the Delivery Catheter

Figure 3:
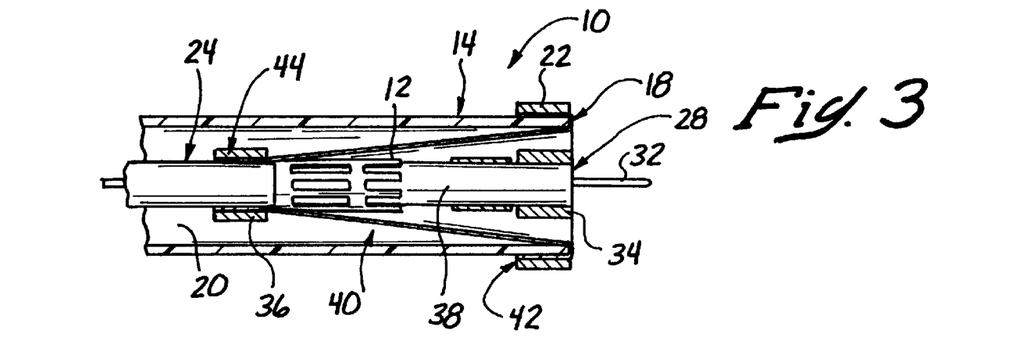
FIG. 3 is a longitudinal-sectional view of the distal portion of the delivery catheter of the present invention, disposed in an initial configuration wherein a radially expandable stent is contained within the delivery catheter.

Referring now to FIGS. 1–3, the delivery catheter 10 comprises an elongate, flexible outer tube 14 which defines a proximal end 16 and a distal end 18. Extending longitudinally through the outer tube 14 is a lumen 20 which is defined by an inner luminal surface of the outer tube 14. Rigidly attached to the outer surface of the outer tube 14 is an annular radiopaque marker 22, the distal edge of which is substantially flush with the distal end 18 of the outer tube 14.

In addition to the outer tube 14, the delivery catheter 10 comprises an elongate, flexible inner tube 24 having a proximal end and a distal end 28. Extending longitudinally through the inner tube 24 is guidewire lumen 30 which is defined by the inner luminal surface of the inner tube 24 and is adapted to accommodate an elongate guidewire 32. As will be discussed in more detail below, in the delivery catheter 10 the inner tube 24 is movably disposed within the lumen 20 of the outer tube 14 so as to allow the inner tube 24 to be distally advanced relative to the outer tube 14 or, alternatively, to allow the outer tube 14 to be proximally retracted relative to the inner tube 24.

Figure 4:
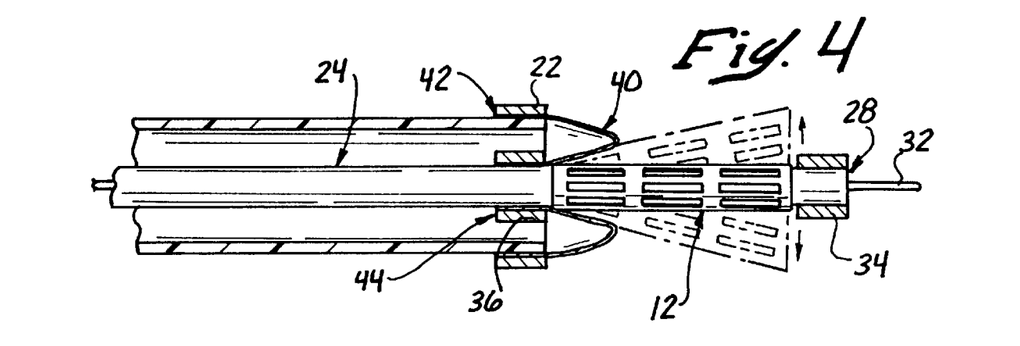
FIG. 4 is a longitudinal-sectional view of the distal portion of the delivery catheter of the present invention, illustrating the manner in which a self-expanding stent is deployed from the distal end thereof.

As seen in FIGS. 2–4, attached to the outer surface of the inner tube 24 is an annular, distal radiopaque marker 34, the distal edge of which is substantially flush with the distal end 28 of the inner tube 24. In addition to the distal radiopaque marker 34, also attached to the outer surface of the inner tube 24 at a location proximal to the distal end 28 is an annular, proximal radiopaque marker 36. In the delivery catheter 10, a distal portion 38 of the inner tube 24 is defined between the distal and proximal radiopaque markers 34, 36. As will also be described in more detail below, the distal portion 38 of the inner tube 24 is adapted to have a vascular stent (e.g., the stent 12) positioned thereupon for deployment into a desired treatment site.

The delivery catheter 10 constructed in accordance with the preferred embodiment of the present invention further comprises a flexible deployment sleeve 40 having a first end 42 which is attached to the outer tube 14 and a second end 44 which attached to the inner tube 24. More particularly, the first end 42 of the sleeve 40 is rigidly captured between the radiopaque marker 22 and the outer surface of the outer tube 14, with the second end 44 of the sleeve 40 being rigidly captured between the proximal radiopaque marker 36 and the outer surface of the inner tube 24. Alternatively, outer tube 14 and sleeve 40 may be made from one piece, (e.g., by thinning and/or expanding the distal segment of the outer tube 14 to form sleeve 40).

Figure 5:
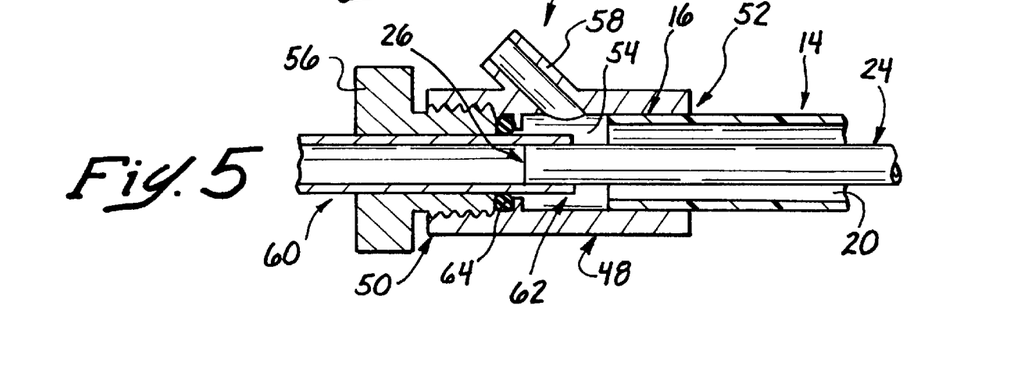
FIG. 5 is a longitudinal-sectional view of the proximal connector assembly of the delivery catheter of the present invention.

Referring now to FIG. 5, attached to the proximal ends 16, 26 of the outer and inner tubes 14, 24 is a proximal connector assembly 46. In the preferred embodiment, the proximal connector assembly 46 comprises a tubular outer body 48 having a proximal end 50, a distal end 52 and an inner surface which defines an interior chamber 54. The proximal portion of the inner surface of the outer body 48 is internally threaded to facilitate the threadable engagement of a knob member 56 to the proximal end 50 of the outer body 48. In the delivery catheter 10, the proximal end 16 of the outer tube 14 is rigidly attached to the distal end 52 of the outer body 48. More particularly, a proximal portion of the outer surface of the outer tube 14 is rigidly secured to a distal portion of the inner surface of the outer body 48. The attachment of the outer tube 14 to the outer body 48 is preferably facilitated through the use of an adhesive, though other bonding techniques may also be employed in the delivery catheter 10. When the outer tube 14 is attached to the outer body 48, the lumen 20 fluidly communicates with the interior chamber 54. The outer body 48 further includes an integral tubular side arm portion 58 which also fluidly communicates with the interior chamber 54, and hence the lumen 20 of the outer tube 14.

The proximal connector assembly 46 of the delivery catheter 10 further comprises a tubular inner body 60 which defines a proximal end and a distal end 62. The inner body 60 is extended through a passage extending axially through the knob member 56, such that the distal end 62 thereof resides within the interior chamber 54 of the outer body 48. The proximal end 26 of the inner tube 24 is rigidly attached to the distal end 62 of the inner body 60. More particularly, a proximal portion of the outer surface of the inner tube 24 is rigidly secured to a distal portion of the inner surface of the inner body 60. The attachment of the inner tube 24 to the inner body 60 is also preferably facilitated through the use of an adhesive, though alternative bonding techniques may also be employed in the delivery catheter 10.

In addition to the aforementioned structural components, the proximal connector assembly 46 further includes an elastically deformable sealing member 64 which is disposed and captured between the inner surface of the outer body 48 and the outer surface of the inner body 60. The sealing member 64 preferably comprises a 0-ring which is compressible, and fabricated from a lubricous material. When captured between the outer and inner bodies 48, 60, the sealing member 64 creates a fluid-tight seal therebetween, thus preventing the escape of any fluid within the interior chamber 54 from the proximal end 50 of the outer body 48 (i.e., from between the outer body 48 and knob member 56).

In the proximal connector assembly 46, the distal end of the knob member 56 is cooperatively engaged to the sealing member 64 such that the tightening of the knob member 56 (i.e., the rotation of the knob member 56 in a clockwise direction) as shown has facilitated the compression of the sealing member 64. The compression of the sealing member 64 causes compressive pressure to be applied to the inner body 60 thereby, thus preventing any movement of the outer and inner tubes 14, 24 relative to each other. In this respect, since the outer tube 14 is attached to the outer body 48 and the inner tube 24 to the inner body 60, maintaining the inner body 60 in fixed relation to the outer body 48 by the compression of the sealing member 64 likewise maintains the outer and inner tubes 14, 24 in fixed relation to each other. Conversely, the loosening of the knob member 56 (i.e., the rotation of the knob member 56 in a counter-clockwise direction) discontinues the application of compressive pressure to the inner body 60 by the sealing member 64, thus permitting the movement of the outer and inner tubes 14, 24 relative to each other. Because compressive pressure is applied thereto, the inner body 60 is preferably of rigid construction so as to resist crushing or collapse when the sealing member 64 is compressed thereagainst. In this respect, the inner body 60 is preferably fabricated from a metal material, though other suitable rigid materials may also be used as an alternative to metal.

Referring now to FIGS. 3 and 4, the delivery catheter 10 is preferably used in conjunction with a self-expanding stent, such as the stent 12 shown in FIGS. 7 and 7a. The delivery catheter 10 is used to deploy the stent 12 into a treatment site by initially positioning the rolled stent 12 upon the distal portion 38 of the inner tube 24. Subsequent to the stent 12 being positioned thereupon, the distal portion 38 is drawn proximally into the lumen 20 of the outer tube 14. The movement of the distal portion 38 into the lumen 20 is facilitated by loosening the knob member 56 of the proximal connector assembly 46, and pulling the inner body 60 proximally while maintaining a tight grasp on the outer body 48, thus resulting in the proximal movement of the inner tube 24 relative to the outer tube 14. When the distal portion 38 (having the stent 12 positioned thereupon) is fully received into the lumen 20, the sleeve 40 is proximally stretched between the outer and inner tubes 14, 24, with the distal radiopaque marker of the inner tube 24 being concentrically positioned relative to the radiopaque marker 22 of the outer tube 14. Additionally, an annular, conically shaped space is defined between the sleeve 40 and the inner luminal surface of the outer tube 14.

Subsequent to the positioning of the distal portion 38 into the lumen 20, the knob member 56 of the proximal connector assembly 46 is re-tightened, thus preventing any movement of the outer and inner tubes 14, 24 relative to each other. The inner tube 24 of the delivery catheter 10 is then advanced over the intraluminally positioned guidewire 32 which is extended into the guidewire lumen 30 of the inner tube 24. The advancement of the inner tube 24, and hence the delivery catheter 10, along the guidewire 32 is continued until such time as the distal end 18 of the outer tube 14 is disposed proximal to a desired treatment site (e.g., a stenosis). Importantly, the distal end 18 of the outer tube 14 is precisely positionable relative to the treatment site due to the inclusion of the radiopaque marker 22 thereon. As will be recognized, due to the knob member 56 of the proximal connector assembly 46 being tightened, the outer and inner tubes 14, 24 move as a unit as the delivery catheter 10 is advanced along the guidewire 32.

As best seen in FIG. 4, subsequent to the placement of the distal end 18 of the outer tube 14 at the desired location relative to the treatment site, the knob member 56 of the proximal connector assembly 46 is once again loosened so as to allow for axial movement of the outer and inner tubes 14, 24 relative to each other. The lumen 20 of the outer tube 14 is then pressurized with a fluid (e.g., sterile saline or contrast media) via the side arm portion 58 of the outer body 48 of the proximal connector assembly 46. The fluid flows into the space defined between the sleeve 40 and the inner luminal surface of the outer tube 14, with fluid pressure being exerted distally against the sleeve 40.

Importantly, the application of distally directed pressure to the sleeve 40 by the fluid within the lumen 20 results in the distal advancement of the distal portion 38 of the inner tube 14 from the distal end 18 of the outer tube 14. In this respect, with the knob member 56 being loosened, the outer body 48 of the proximal connector assembly 46 is tightly grasped as the lumen 20 is pressurized with the fluid, thus allowing for the movement of the inner tube 24 distally relative to the outer tube 14. The distal advancement of the inner tube 24 from the distal end 18 of the outer tube 14 is continued until such time as the proximal radiopaque marker 36 of the inner tube 24 is concentrically positioned relative to the radiopaque marker 22 of the outer tube 14. As will be recognized, once the radiopaque markers 22, 36 are concentrically oriented relative to each other, the stent 12 positioned upon the distal portion 38 is completely uncovered and is no longer surrounded by the outer tube 14.

In applications where the stent 12 is of the self-expanding variety, the stent 12 immediately expands radially outwardly into engagement with the luminal surface of the anatomical passageway upon being removed from within the lumen 20 of the outer tube 14 in the aforementioned manner. Reference to the radiopaque markers 22, 34, 36 allows for confirmation of the proper orientation of the stent 12 relative to the treatment site. Subsequent to the deployment of the stent 12, the knob member 56 of the proximal connector assembly 46 is re-tightened, and the delivery catheter 10 may then be withdrawn from over the guidewire 32.

It is contemplated that the delivery catheter 10 incorporating the self-expanding stent 12 may also be used by initially orienting the distal end 18 of the outer tube 14 distal to the desired treatment site. In this respect, subsequent to the loosening of the knob member 56 of the proximal connector assembly 46, the inner body 60 (rather than the outer body 48) is tightly grasped. Thus, the pressurization of the lumen 20 of the outer tube 14 in the aforementioned manner causes the outer tube 14 to be proximally retracted relative to the inner tube 24. The proximal retraction of the outer tube 14 relative to the inner tube 24 is continued until such time as the radiopaque marker 22 of the outer tube 14 is concentrically positioned relative to the proximal radiopaque marker 36 of the inner tube 24, thus indicating that the distal portion 38 of the inner tube 24 (including the stent 12 positioned thereupon) has been fully removed from within the lumen 20 of the outer tube 14.

Figure 4A:
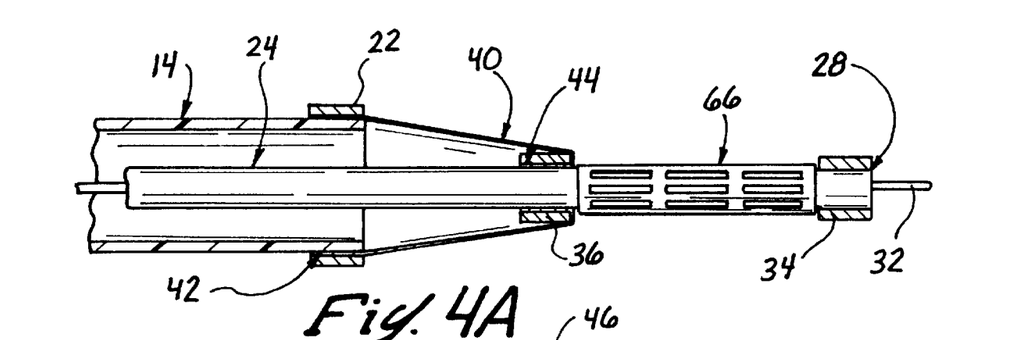
FIG. 4a is a longitudinal-sectional view of the distal portion of the delivery catheter of the present invention, illustrating the manner in which a pressure expandable stent is deployed from the distal end thereof.

Referring now to FIGS. 2 and 4a, the delivery catheter 10 of the present invention may be used in conjunction with a pressure expandable stent 66 rather than with the self-expanding stent 12. If the delivery catheter 10 is to be used in conjunction with the pressure expandable stent 66, the inner tube 24 thereof is modified to include an inflatable balloon 68 which is disposed upon the distal portion 38 between the distal and proximal radiopaque markers 34, 36.

The delivery catheter 10 incorporating the balloon 68 and the pressure expandable stent 66 is used in substantially the same manner as previously described in relation to the delivery catheter 10 incorporating the self-expanding stent 12. In this respect, the pressure expandable stent 66 is positioned over and collapsed about the balloon 68, with the inner tube 24 then being moved proximally relative to the outer tube 14 so as to draw the distal portion 38 (including the balloon 68 having the stent 66 positioned thereupon) into the lumen 20 of the outer tube 14, as seen in FIG. 2. As seen in FIG. 4a, subsequent to the positioning of the radiopaque marker 22 proximal to the treatment site, the stent 66 is deployed from within the lumen 20 of the outer tube 14 in essentially the same manner as previously described in relation to the deployment of the stent 12 therefrom. Thereafter, the balloon 68 is inflated, thus facilitating the radial expansion of the stent 66 into contact with the luminal surface of the anatomical passage. The balloon 68 is then deflated, and the delivery catheter may be removed as described above.

ii. Rapid Exchange Embodiments of the Delivery Catheter

Figure 6:
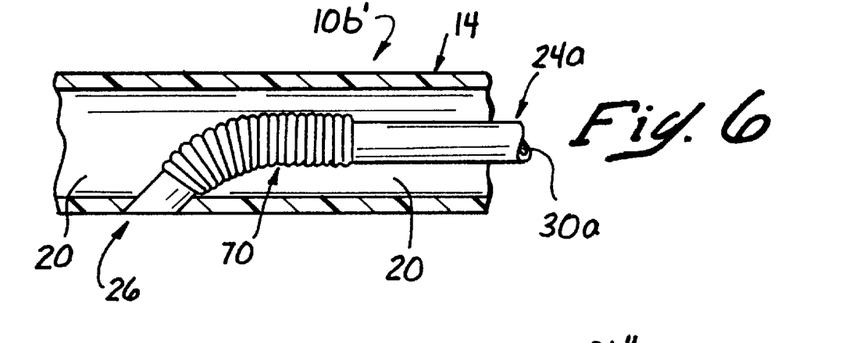
FIG. 6 is a partial longitudinal-sectional view of a first alternative embodiment of the delivery catheter.

Referring now to FIG. 6, the delivery catheter 10 of the present invention may alternatively be configured to incorporate an inner tube 24a having a proximal end 26 which is attached to the outer tube 14 such that the guidewire lumen 30a of the inner tube 24a communicates with the outer surface of the outer tube 14. As will be recognized, if the inner tuber 24a is incorporated into the delivery catheter 10, the proximal connector assembly 46 will have a modified configuration, with only the proximal end of the outer tube 14 being attached thereto.

Though not shown, the distal region of the inner tube 24a is identically configured to that of the previously described inner tube 24, and includes a distal portion defined between distal and proximal radiopaque markers, with the distal portion being adapted to have a self-expanding stent positioned thereupon, or being provided with an inflatable balloon for use with a pressure expandable stent. Additionally, the opposed ends of a flexible sleeve are attached to and extend between the outer tube 14 and the inner tube 24a in the same manner as previously described in relation to the sleeve 40 and outer and inner tubes 14, 24.

When the delivery catheter 10 incorporates the inner tube 24a, the deployment of either a self-expanding stent or a pressure expandable stent from within the lumen 20 of the outer tube 14 is facilitated by the distal advancement of the distal portion of the inner tube 24a from the distal end 18 of the outer tube 14. Since the proximal end 26a of the inner tube 24a is rigidly secured to the outer tube 14, such distal advancement is accomplished by providing the inner tube 24a with an expandable region 70 preferably having a bellows-like configuration. In this respect, when the lumen 20 of the outer tube 14 is pressurized with the fluid, distally directed fluid pressure is exerted against the sleeve, thus causing the longitudinal stretching of the expanded region 70. Such stretching of the expanded region 70 allows the inner tube 24a to move distally relative to the outer tube 14, and thus facilitates the distal advancement of the distal portion of the inner tube 24a from the distal end 18 of the outer tube 14. The expandable region 70 is preferably sized such that when fully stretched, the distal portion of the inner tube 24a bearing the stent is completely removed from within the lumen 20 of the outer tube 14.

Figure 6A:
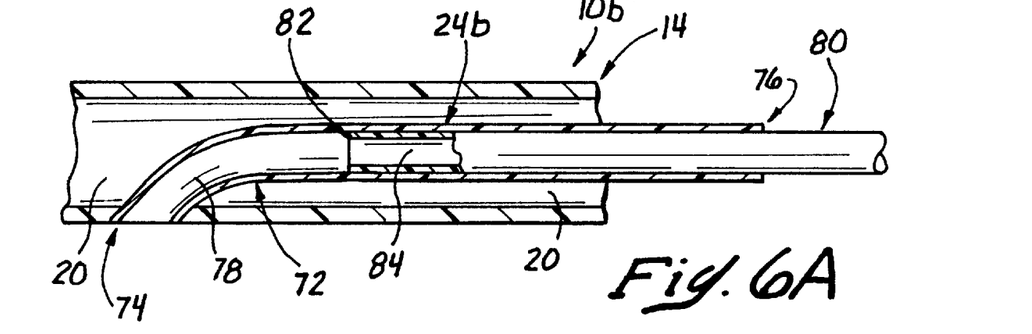
FIG. 6a is a partial longitudinal-sectional view of a first alternative embodiment of the delivery catheter with the distal portion of the inner tube not surrounded laterally by the outer tube.

Referring now to FIG. 6a, as an alternative to the inner tube 24a, the delivery catheter 10 may be provided with an inner tube 24b. The inner tube 24b comprises a tubular outer sleeve 72 having a proximal end 74 and a distal end 76. The proximal end 74 of the outer sleeve 72 is rigidly secured to the outer tube 14 such that the lumen 78 of the outer sleeve 22 communicates with the outer surface of the outer body 14. In addition to the outer sleeve 72, the inner tube 24b includes a tubular inner sleeve 80 having a proximal end 82 and a distal end. Though not shown, the distal region of the inner sleeve 80 is identically configured to the distal region of the inner tube 24.

In the inner tube 24b, the proximal end 82 of the inner sleeve 80 is disposed within the lumen 78 of the outer sleeve 72 and slidably movable therewithin. The inner sleeve 80 itself defines a lumen 84 which communicates with the lumen 78 of the outer sleeve 72 when the outer and inner sleeves 72, 80 are slidably attached to each other in the aforementioned manner. Importantly, when the lumen 20 of the outer tube 14 is pressurized with the fluid, the distally directed pressure exerted against the sleeve results in the sliding movement of the inner sleeve 80 distally relative to the outer sleeve 72. Such distal movement of the inner sleeve 80 facilitates the distal advancement of the distal portion thereof from the distal end 18 of the outer tube 14. The overlap between the outer and inner sleeves 72, 80 is sized such that the inner sleeve 80 may be distally moved relative to the outer sleeve 72 in an amount sufficient to facilitate the complete removal of the distal portion of the inner sleeve 80 bearing the stent from within the lumen 20 of the outer tube 14.

Figure 8A:
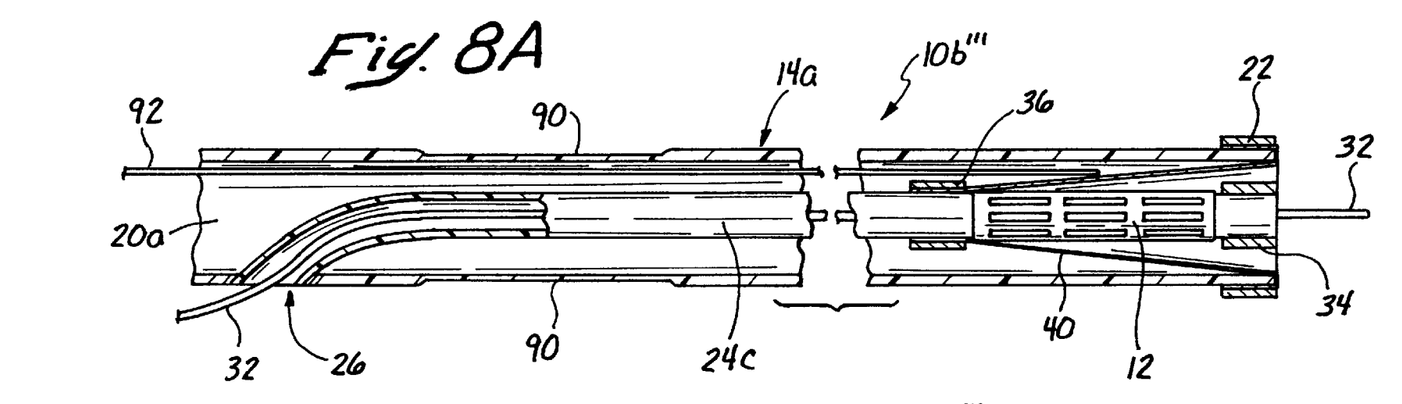
FIG. 8a is a longitudinal-sectional view of a distal portion of a second alternative embodiment of the delivery catheter disposed in an initial configuration wherein a radially expandable stent is contained within the lumen of the delivery catheter.
Figure 8B:
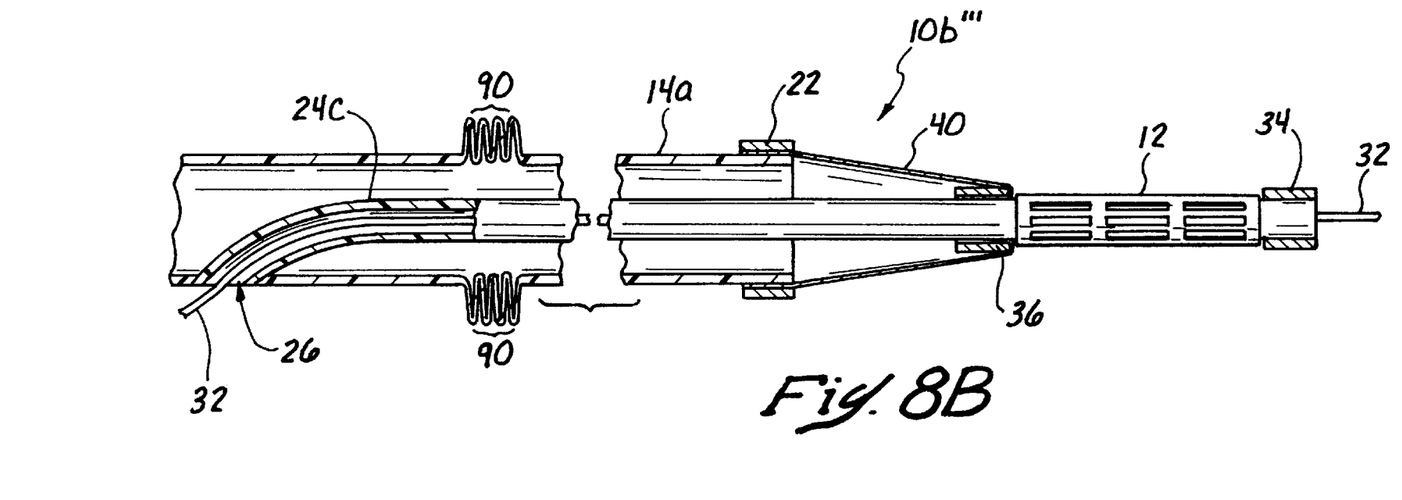
FIG. 8b is a longitudinal-sectional view of the second alternative embodiment of the delivery catheter shown in FIG. 8a, disposed in a deployment configuration wherein the stent is positioned outboard of the catheter.

A second alternative embodiment of the delivery catheter 10 is shown in FIGS. 8a and 8b. This second alternative embodiment comprises an elongate pliable outer tube 14a which has a collapsible segment 90. The collapsible segment 90 of the outer tube 14a may be formed of a plastic film or membrane bonded to separate segments of the outer tube 14a, or as shown in the drawings may comprise a portion of the outer tube 14a which has been drawn or otherwise reduced to a wall thickness which is narrower than that of the remainder of the outer tube 14a so as to permit folding or pliability of that collapsible segment 90. Scored regions, living hinges or relatively pliable areas may be formed in the collapsible segment 90 to cause the collapsible segment 90 to longitudinally collapse or fold in a zig-zag (e.g., "accordion" type) manner, as shown in FIG. 8b.

The inner tube 24 of this alternative embodiment is a continuous, non-telescoping, non-collapsible tubular member having a proximal end anchored to the outer tube 14a at the side opening 26 and a distal end whereupon the stent 12 is mounted.

Depending on the relative structural integrity and rigidity of the collapsible segment 90 of the outer tube 14a, it may be desirable to provide an optional stiffening member 92, such as a wire, within the lumen 20a of the outer tube. Such stiffening member 92 will be disposed within the lumen 20a of the outer tube 14a when this alternative embodiment of the catheter 10 is in its initial configuration shown in FIG. 8a, wherein the stent 12 is positioned within the lumen 20a of the outer tube 14a. the stiffening member 92 will prevent the outer tube 14a from bending or sagging in the region of the collapsible segment 90 when the outer tube 14a is in its elongated configuration shown in FIG. 8a. In the elongated configuration, the delivery catheter is then advanced through the vasculature until the positions of the proximal and distal radiopaque markers 36, 34 indicate that the stent 12 is located at its desired position within the vasculature.

Thereafter, stiffening member 92 is removed. Lumen 20a of the outer tube 14a is then pressurized with blood thereby causing the distal segment of the outer tube 14a to move proximally and the collapsible segment 90 assumes the collapsed (e.g., folded, compressed) configuration as shown in proximal movement of FIG. 8b. Such shortening of the outer tube 14a and proximal movement of the distal end of the outer tube 14a expose the stent 12 as shown in FIG. 8b. In embodiments wherein the stent 12 is of the pressure expandable variety, a balloon inflation fluid or other force is then used to exert outward radial pressure against the stent 12 to radially expand the stent into contact with the surrounding luminal surface. In other embodiments wherein the stent 12 is of the self-expanding variety, the mere removal of the constraint of the outer tube 14a from the stent 12 will allow the stent 12 to self-expand to its desired radially expanded configuration in contact with the luminal surface of the surrounding blood vessel wall.

The delivery catheters constructed in accordance with the present invention provide numerous advantages over stent delivery systems known in the prior art. In prior art delivery systems, a sheath must be manually moved relative to a delivery catheter to facilitate the deployment of the stent. As such, the materials of the sheath and the delivery catheter must be thick walled and/or stiff. Such designs result in the catheter delivery system being too stiff or bulky to be effectively used in small vessels and/or tortuous anatomical passageways. The present delivery system uses fluid pressure to deploy the stent from the delivery catheter. As such, the stent deployment using the present delivery system is conducted in a much more controlled manner, with the present design allowing for the use of very thin-walled and flexible materials for the outer and inner tubes 14, 24. The use of such materials results in a delivery system that is smaller and significantly more flexible than those known in the prior art.

iii. A Preferred Roll-Up Stent

FIGS. 7 and 7a show a preferred stent 12 which may be used with the preferred delivery catheter 10, or with any other suitable delivery catheter or delivery device. The preferred stent 12 is formed of a biocompatable material, and is fabricated by milling or chemically etching a rectangularly configured, thin-walled sheet 86 such that a desired pattern of elongate slots 88, each of which defines a longitudinal axis, are formed in the sheet 86. The preferred pattern of the slots 88 consists of a series of rows, with the longitudinal axes of the slots 88 in each row being linearly aligned with each other and extending in parallel relation to the longitudinal axes of the slots 88 in the remaining rows. The sheet 86 has a preferred thickness of from approximately 0.0005 inches to 0.004 inches. Subsequent to the slots 88 being formed therein, the sheet 86 is rolled longitudinally into the tubular shape shown in FIG. 7a. The pattern of the slots 88 within the sheet 86 will typically be varied according to the intended application of the stent 12. In this respect, the pattern of the slots 88 shown in FIG. 7 is preferred when the stent 12 is to be used in relation to blood flow applications since, as seen in FIG. 7a, the longitudinal axes of the slots 88 will be parallel to the direction of blood flow when the stent 12 is operatively positioned, thus promoting laminar blood flow therethrough. The sheet 86 may be fabricated from a radiopaque material, or may have radiopaque markers embedded therein.

This stent 66 may be self-expanding or pressure- expandable. In self expanding embodiments, the sheet 86 will typically be formed of resilient or shape memory material.

Examples of shape memory materials which may be used include Nickel-Titanium alloys (e.g., Nitinol) which exist in a first crystalline state (e.g. austinite) having a radially compact shape below a certain transition temperature and a second crystalline state (e.g., martinsite) having the radially expanded shape above that transition temperature. In some applications the particular shape memory material may be selected so that its transition temperature is at or near body temperature (e.g. 37 degrees C. in humans) such that the stent will self-expand after it has been introduced into the body, and any expansion-preventing restraint (e.g., sheath, clip, surrounding catheter wall, etc.) has been removed.

In other applications, the transition temperature of the shape memory material may be below body temperature (e.g. approx. 37 degrees C.) such that the stent may be initially formed at a temperature below its transition temperature, and subsequently allowed to its second crystalline state (and its radially expanded configuration) before it is fully warmed to body temperature. In these particular embodiments at least, the shape memory material will have elastic or superelastic properties while in its second crystalline state, and the stent 12 will be mounted on the delivery catheter in its radially compact configuration and will be restrained and held in its radially compact configuration by the outer tube 14 or by a retractable clip or other holding apparatus associated with the delivery catheter 10. Thereafter, when it is desired to allow the stent 12 to self-expand, the outer tube 14 will be retracted or the inner tube 24 will be advanced, or the other holding apparatus (e.g. retractable clip) will be released—thereby allowing the stent 12 to assume its radially expanded configuration.

Alternatively to shape memory materials, the stent 12 may be fabricated from any other malleable (pressure expandable) or resilient (self-expanding) material, such as wire, perforated metal or plastic, or various other materials.

iv. Inflation Pump/Retractor Apparatus

FIG. 9 shows an inflation pump/retractor apparatus 100 which is useable in conjunction with the rapid exchange embodiment of the delivery catheter 10b''' shown in FIG. 8a which incorporates a stiffening element 92 attached to the wall of the outer tube 14 at a location distal to its collapsible segment 90.

The inflation pump/retractor apparatus 100 comprises a housing 102 having a hollow bore 104 formed therein, and a fluid outlet opening 106 which is connectable or couplable (e.g., by way of a tube) to the lumen 20a of the outer tube 14a. A first set of threads 108 are formed on the proximal portion of the inner wall of the housing 104. A plunger 110 has a second set of threads 112 formed about the outer surface thereof, and such second set of threads 112 are engaged with the first set of threads 108 of the housing, such that rotation of the plunger 110 in a first (e.g., clockwise) direction will cause the plunger to advance in the distal direction DD within the bore 104 of housing 102, and rotation of the plunger 110 in a second direction (e.g., counterclockwise) will cause the plunger to withdraw in the proximal direction PD within the bore 104 of housing 102. An annular seal member 114 is formed on the plunger 110, and slides in substantially fluid tight contact with the inner wall of the bore 104 of housing 102 such that, when the plunger 110 is advanced in the distal direction DD, fluid contained within the bore 104 of the housing 102 will be expelled through opening 106 and into the lumen 20a of the outer tube 14a, thereby increasing the pressure within the lumen 20a of the outer tube 14a to urge the rapid exchange delivery catheter 10b''' to transition from its first configuration (i.e., distal portion of inner tube 24a or 24b within lumen 20a of outer tube 14a) to its second configuration (i.e., distal portion of outer tube 14a retracted proximally so as to expose the distal portion of inner tube 24c).

Additionally, the stiffening member 92 is attached to the outer tube 14a at a location which is distal to the collapsible segment 90. The proximal portion of this stiffening member 92 extends through opening 106, and through the bore 104, as shown.

A hollow passageway 120 is formed longitudinally through the plunger 110, preferably at the center thereof, and the proximal end of the stiffening element 92 protrudes at least partially through that passageway 120. A third set of threads 122 is formed about the inner surface of the passageway 120. This third set of threads 122 are formed in an opposite helical direction to the first set of threads 108 formed on the inner surface of the housing 102. (i.e., "reverse threaded") A threaded bushing 124, having a fourth set of threads 126 formed about the outer surface thereof, is nonrotatably mounted or formed on the stiffening element 92. The fourth set of threads 126 formed on the bushing 124 are engaged with the third set of threads 122 formed inside the passageway 120 of the plunger 110. In this manner, when the plunger 110 is rotated in the first direction (e.g., clockwise) so as to advance the plunger 110 in the distal direction, the bushing 124 will ride in the proximal direction upon the third set of threads 122, thereby pulling or retracting the stiffening element 92 in the proximal direction PD. Preferably the rate at which the stiffening element 92 is pulled in the proximal direction PD is equivalent to or otherwise coordinated with the rate at which the plunger advances in the distal direction to cause a.) the infusion of fluid into the lumen 20 of the outer tube 14a and b.) the retraction of the stiffening element 92 to occur simultaneously, and in a coordinated fashion, so as to bring about smooth transitioning of the catheter 10b''' from its first configuration to its second configuration.

In some applications, it may be desirable to retransition the delivery catheter 10b''' from its second configuration back to its first configuration after the radially expandable apparatus has been implanted within the body. This can be accomplished by rotating the plunger 110 in the second (e.g., counterclockwise) direction so as to cause a.) withdrawal of fluid from the lumen 20a of the outer tube 14a concurrently with b.) advancement of the stiffening element 92 in the distal direction DD, thereby returning the delivery catheter 10b''' to its first configuration.

It is to be appreciated that various additions, deletions, modifications and alterations may be made to the above described preferred embodiments without departing from the intended spirit and scope of the invention. Thus, the particular combination of parts described and illustrated herein is intended to represent only certain embodiments of the present invention, and is not intended to serve as limitations of alternative devices within the spirit and scope of the invention.

What is claimed is:

1. A delivery catheter for delivering a radially expandable intraluminal apparatus to a desired location within a body lumen, said catheter comprising:

a) an outer tube having a proximal end, a distal end, and a lumen extending longitudinally therethrough;

b) an inner tube having a proximal end, a distal end, and a lumen extending longitudinally therethrough, said inner tube being disposed within the lumen of the outer tube, said inner tube having a distal portion upon which the intraluminal apparatus may be mounted; and c) a flexible sleeve having a first end attached to a distal portion of the outer tube and a second end attached to the inner tube at a location which is proximal to said distal portion of said inner tube, said sleeve forming a substantially fluid-tight seal between said inner tube and said outer tube;

d) at least a portion of one of said inner and outer tubes being longitudinally moveable relative to the other thereof such that by changing the fluid pressure within the lumen of the outer tube, the delivery catheter will be caused to transition between:
   i) a first configuration wherein the distal portion of the inner tube is surrounded laterally by the outer tube; and
   ii) a second configuration wherein the distal portion of the inner tube is not surrounded laterally by said outer tube; and e) a guidewire opening formed in the outer tube at a location between its proximal and distal ends, and the proximal end of the inner tube is affixed to the wall of the outer tube such that said guidewire opening leads to into the lumen of the inner tube, said inner tube thereby extending though only that portion of the lumen of the outer tube which extends from the guidewire opening to the distal end of the outer tube, and one of said inner and outer tubes being of variable length to facilitate the transitioning of the delivery catheter between its first configuration and its second configuration while the proximal end of the inner tube remains affixed to the wall of the outer tube.

2. The delivery catheter of claim 1 wherein said outer tube includes a radiopaque marker attached to the distal end thereof.

3. The delivery catheter of claim 2 wherein the first end of the sleeve is rigidly captured between said radiopaque marker and said outer tube.

4. The delivery catheter of claim 1 wherein the outer tube and the sleeve are made from one piece.

5. The delivery catheter of claim 1 wherein said inner tube includes a distal radiopaque marker attached to the distal end thereof and a proximal radiopaque marker attached thereto at a location proximal to the distal end thereof, the distal portion of the inner tube being defined between the distal and proximal radiopaque markers.

6. The delivery catheter of claim 5 wherein the second end of the sleeve is rigidly captured between the proximal radiopaque marker and the inner tube.

7. The delivery catheter of claim 1 further in combination with a self-expanding vascular stent positioned on the distal portion of the inner tube.

8. The delivery catheter of claim 1 further comprising an inflatable balloon disposed on the distal portion of the inner tube.

9. The delivery catheter of claim 8 further in combination with a pressure-expandable vascular stent positioned on the inflatable balloon.

10. The delivery catheter of claim 1 further comprising a proximal connector assembly attached to the proximal ends of the inner and outer tubes, said proximal connector assembly comprising:

a tubular outer body defining proximal and distal ends, the proximal end of the outer tube being attached to the distal end of the outer body;

a knob member rotatably connected to the proximal end of the outer body;

a tubular inner body defining proximal and distal ends, said inner body extending through the knob member and into the outer body, the proximal end of the inner tube being attached to the distal end of the inner body; and an elastically deformable sealing member disposed between the inner and outer bodies;

said knob member being cooperatively engaged to the sealing member such that the rotation of the knob member in a first direction causes compressive pressure to be applied to the inner body by the sealing member which prevents the movement of the inner and outer tubes relative to each other, and the rotation of the knob member in a second direction opposite the first direction discontinues the application of the compressive pressure to the inner body by the sealing member which permits the movement of the inner and outer tubes relative to each other.

11. The delivery catheter of claim 10 wherein said outer body includes a tubular side arm portion which fluidly communicates with the lumen of the outer tube.

12. An over-the-wire embodiment of the delivery catheter of claim 1 wherein the inner tube extends substantially through the entire length of the outer tube and is axially moveable therewithin.

13. The delivery catheter of claim 1 wherein the variability in length of said at least one of said inner and outer tubes is by way of a collapsible segment formed therein.

14. The delivery catheter of claim 1 wherein the variability in length of said at least one of said inner and outer tubes is by way of a telescoping segment formed therein.

15. The delivery catheter of claim 1 wherein the outer tube is variable in length and the inner tube is of fixed length.

16. The delivery catheter of claim 15 further comprising a stiffening element which extends through said outer tube and which is attached to the outer tube such that pulling on the stiffening element in the proximal direction will assist the delivery catheter in transitioning from its first configuration to its second configuration.

17. A system comprising the delivery catheter of claim 16 in combination with an infusion pump/retractor apparatus, said infusion pump/retractor apparatus being connected to the lumen of the outer tube and to said stiffening element and being operative to infuse inflation fluid into the lumen of the outer tube while concurrently exerting proximally directed pulling force on the stiffening element, thereby causing the delivery catheter to transition from its first configuration to its second configuration.

18. The system of claim 17 wherein the infusion pump/retractor apparatus comprises:

a housing having a hollow bore extending longitudinally therethrough, said bore being defined by an inner housing surface;

a fluid outlet opening formed in said housing and coupled to the lumen of the outer tube of said delivery catheter such that fluid contained within the bore of the housing may be expelled through said fluid outlet opening and into the lumen of the outer tube;

a first set of threads formed on the inner housing surface of said housing;

a plunger received within the bore of said housing, said plunger having a sealing member which is in substantially fluid tight sealing contact with the inner housing surface, said plunger being longitudinally moveable within said housing such that when said plunger is advanced in the distal direction fluid will be expelled through the fluid outlet opening into the lumen of the outer tube;

a second set of threads being formed on said plunger, said second set of threads being engaged with said first set of threads such that rotation of said plunger in a first direction will cause the plunger to advance distally within the bore of the housing;

a hollow passageway defined by an inner plunger surface and extending longitudinally through the plunger, said stiffening element extending at least part way into said hollow passageway;

a third set of threads formed on the inner plunger surface, said third set of threads being in a direction which is opposite to the direction of the first set of threads formed on said inner housing surface;

a fourth set of threads formed on said stiffening element, said fourth set of threads being engaged with the third set of threads formed on said inner plunger surface such that, as said plunger is rotated in said first direction, the stiffening element will be retracted in the proximal direction.

19. The system of claim 18 wherein said first, second, third and fourth sets of threads are configured relative to one another to cause the proximally directed retraction of the stiffening element to be coordinated with the infusion of fluid into the lumen of the outer tube, thereby facilitating smooth transitioning of the deliver catheter from its first configuration to its second configuration.

20. The delivery catheter of claim 1 wherein the inner tube is variable in length and the outer tube is of fixed length.

21. The delivery catheter of claim 1 further comprising a stiffening element which extends through the delivery catheter to prevent unwanted curvature of the catheter.

22. The delivery catheter of claim 21 wherein the stiffening element extends through the lumen of the outer tube.

23. The delivery catheter of claim 22 wherein the outer tube has a longitudinally collapsible segment formed therein and wherein the stiffening element is operative to prevent the outer tube from inadvertently bending in the region of said collapsible segment.

24. A method for implanting a radially expandable endoluminal apparatus at a desired site within a luminal anatomical structure within the body of a mammal, said method comprising the steps of:

(a) providing a delivery catheter which includes:
  i.) an outer tube having a proximal end, a distal end, and a lumen extending longitudinally therethrough;
  ii.) an inner tube having a proximal end, a distal end, and a lumen extending longitudinally therethough, said inner tube being disposed within the lumen of the outer tube;
  iii.) a radially expandable endoluminal apparatus mounted in a radially nonexpandable state upon a distal portion of the inner tube;
  iv.) a flexible sleeve having a first end attached to a distal portion of the outer tube and a second end attached to the inner tube at a location which is proximal to said distal portion of said inner tube, said sleeve forming a substantially fluid-tight seal between said inner tube and said outer tube;
  v.) at least a portion of one of said inner and outer tubes being longitudinally moveable relative to the other thereof such that by changing the fluid pressure within the lumen of the outer tube, the delivery catheter will be caused to transition between:
    a first configuration wherein the distal portion of the inner tube is surrounded laterally by the outer tube; and
    a second configuration wherein the distal portion of the inner tube is not surrounded laterally by said outer tube; and
  vi.) a guidewire opening formed in the outer tube at a location between its proximal and distal ends, and the proximal end of the inner tube is affixed to the wall of the outer tube such that said guidewire opening leads to into the lumen of the inner tube, said inner tube thereby extending though only that portion of the lumen of the outer tube which extends from the guidewire opening to the distal end of the outer tube, and one of said inner and outer tubes being of variable length to facilitate the transitioning of the delivery catheter between its first configuration and its second configuration while the proximal end of the inner tube remains affixed to the wall of the outer tube;

(b) inserting the delivery catheter disposed into the body, with the delivery catheter disposed in its first configuration, and advancing the delivery catheter to a position wherein the distal end of the outer tube is at a desired location relative to the site at which the endoluminal prosthesis is to be implanted;

(c) pressurizing the lumen of the outer tube with a fluid so as to cause the delivery catheter to transition from its first configuration to its second configuration;

(d) causing the endoluminal apparatus to expand radially into contact with the luminal anatomical structure and to separate from the delivery catheter; and (e) removing the delivery catheter from the mammalian body while allowing the endoluminal apparatus to remain implanted therein.

25. The method of claim 24 wherein the radially expandable endoluminal apparatus is of a type which self-expands to its second configuration and is held in its non-expanded state by at least one restraining member while mounted on the distal portion of the inner tube, and wherein step (d) comprises removing said restraining member to allow said apparatus to self expand to its second configuration.

26. The method of claim 24 wherein said outer tube acts as a restraining member to prevent radial expansion of the apparatus while it is within the catheter, and wherein the transitioning of the delivery catheter to its second configuration in step (c) serves to remove the constraint of said restraining member from said apparatus such that the radial expansion of the apparatus in step (d) occurs without further volitional manipulation of the delivery catheter.

27. The method of claim 24 wherein the delivery catheter provided in step (a) further comprises at least one clip for holding the radially expandable endoluminal apparatus in its non-expanded state upon said inner tube, and wherein step (d) of the method comprises releasing said at least one clip so as to allow said apparatus to self-expand.

28. The method of claim 24 wherein the endoluminal apparatus is of the pressure-expandable type and wherein the delivery catheter provided in step (a) further comprises a pressure exerting member for applying outwardly directed radial pressure against said endoluminal apparatus to radially expand said endoluminal apparatus, and wherein step (d) comprises utilizing said pressure exerting member to cause radial expansion of said endoluminal apparatus.

29. The method of claim 28 wherein said pressure exerting apparatus is a balloon positioned on the distal portion of the inner tube, beneath the endoluminal apparatus when said endoluminal apparatus is mounted on said distal portion of said inner tube, and wherein step (d) comprises inflating said balloon to cause radial expansion of said endoluminal apparatus.

30. The method of claim 24 wherein step (c) comprises causing the distal end of the outer tube to retract in the proximal direction.

31. The method of claim 24 wherein step (c) comprises causing the inner tube to extend out of and beyond the distal end of the outer tube.

\* \* \* \* \*